(12) United States Patent
Fink et al.

(10) Patent No.: US 6,943,190 B2
(45) Date of Patent: Sep. 13, 2005

(54) METHOD OF USING PYRUVATE AND/OR ITS DERIVATIVES FOR THE TREATMENT OF CYTOKINE-MEDIATED INFLAMMATORY CONDITIONS

(75) Inventors: Mitchell P. Fink, Pittsburgh, PA (US); Luis Ulloa, Jackson Heights, NY (US); Kevin J. Tracey, Old Greenwich, CT (US); Russell L. Delude, Pittsburgh, PA (US)

(73) Assignees: University of Pittsburgh-of the Commonwealth System of Higher Education, Pittsburgh, PA (US); North Shore-Long Island Jewish Research Institute, Great Neck, NY (US)

(*) Notice: Subject to any disclaimer, the term of this patent is extended or adjusted under 35 U.S.C. 154(b) by 47 days.

(21) Appl. No.: 10/662,975

(22) Filed: Sep. 15, 2003

(65) Prior Publication Data

US 2004/0110833 A1 Jun. 10, 2004

Related U.S. Application Data

(63) Continuation of application No. PCT/US02/08283, filed on Mar. 15, 2002.
(60) Provisional application No. 60/276,279, filed on Mar. 15, 2001.

(51) Int. Cl.[7] .............................................. A61K 31/22
(52) U.S. Cl. ..................................................... 514/456
(58) Field of Search ......................................... 514/546

(56) References Cited

U.S. PATENT DOCUMENTS

| | | |
|---|---|---|
| 4,970,143 A | 11/1990 | Guidoux et al. |
| 5,210,098 A | 5/1993 | Nath |
| 5,354,771 A | 10/1994 | Walser |
| 5,480,909 A | 1/1996 | Stanko |
| 5,648,380 A | 7/1997 | Martin |
| 5,756,469 A | 5/1998 | Beale |
| 5,798,388 A | 8/1998 | Katz |
| 5,908,611 A | 6/1999 | Gottlieb et al. |
| 6,051,609 A | 4/2000 | Yu et al. |
| 6,086,789 A | 7/2000 | Brunengraber et al. |
| 6,417,231 B1 * | 7/2002 | Greenway et al. .......... 514/546 |
| 2003/0073743 A1 * | 4/2003 | Ajami et al. ................ 514/546 |

FOREIGN PATENT DOCUMENTS

WO    WO 00/69431    11/2000

* cited by examiner

Primary Examiner—Raymond J. Henley, III
(74) Attorney, Agent, or Firm—Hamilton Brook Smith & Reynolds, P.C.

(57) ABSTRACT

This invention is directed to a method of using a therapeutic composition comprising a compound of an alpha-ketoalkanoic acid (pyruvate) and/or its derivatives for the treatment of cytokine-mediated inflammatory conditions. The compound is an alpha-ketoalkanoic acid, a physiologically acceptable salt of an alpha-ketoalkanoic acid, an ester of an alpha-ketoalkanoic acid, or an amide of an alpha-ketoalkanoic acid. A component for inducing and stabilizing the enol resonance form of the ester at physiological pH values is also disclosed. The cytokine-mediated inflammatory conditions are mediated by, for example, an "early" (Tumor Necrosis Factor (TNF), interleukin-1β (IL-1β)) or "late" (high mobility group B-1 (HMGB-1)) mediator of inflammation. Exemplary cytokine-mediated inflammatory conditions include, but are not limited to, local and systemic inflammation, inflammatory bowel disease (Crohn's disease and ulcerative colitis), rheumatoid arthritis, asthma (including status asthmaticus), sepsis or septic shock, also including inflammatory skin conditions, for example, psoriasis and eczema.

23 Claims, 7 Drawing Sheets

$R^1$ = methyl, ethyl, propyl, isopropyl, n-butyl, sec-butyl, isobutyl, terbutyl, pentyl, 4-methylpentyl, 3-methylpentyl, hexyl, heptyl, octyl, 1-phenylmethyl, 2-phenyl-ethyl $R^2$ = ethyl, propyl, isopropyl, n-butyl, sec-butyl, isobutyl, terbutyl, pentyl, 4-methylpentyl, ethoxymethyl, 2-ethoxyethyl, carboxymethyl, ethoxycarbonylmethyl

*FIG. 1A*

R is alkyl group

$R^1$ and $R^2$ are independently H, alkyl, aralkyl, alkoxyalkyl, carboxyalkyl, -CHR3COOH $R^3$ is the side chain of a naturally occurring amino acid

TNF mRNA

FIG. 5B

LPS Time - | 15 min | - | 4 hours |
[EP] (mM) - - 1 5 - - 1 5

[LPS] (ng/ml) - | 50 | 100 |
[EP] (mM) - - 1 5 10 - - 1 5 10

Phospho - p38 MAPK

*FIG. 6C*

Total p38 MAPK

```
SEQUENCE LISTING

<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: sense primer for murine NF-KB

<400> SEQUENCE: 1
agttgagggg actttcccag gc                                              22

<210> SEQ ID NO 2
<211> LENGTH: 22
<212> TYPE: DNA
<213> ORGANISM: Artificial Sequence
<220> FEATURE:
<223> OTHER INFORMATION: anti-sense primer for murine NF-KB

<400> SEQUENCE: 2
gcctgggaaa gtcccctcaa ct                                              22
```

METHOD OF USING PYRUVATE AND/OR ITS DERIVATIVES FOR THE TREATMENT OF CYTOKINE-MEDIATED INFLAMMATORY CONDITIONS

RELATED APPLICATIONS

This application is a continuation of International Application No. PCT/US02/08283, which designated the United States and was filed on Mar. 15, 2002, published in English, which claims the benefit of U.S. Provisional Application No. 60/276,279, filed on Mar. 15, 2001. The entire teachings of the above applications are incorporated herein by reference.

GOVERNMENT SUPPORT

The invention was supported, in whole or in part, by a grant ROI GM57226-02 from the National Institute of Health and by a grant N65236-00-1-5434 from the Defense Advanced Research Projects Agency (DARPA). The Government has certain rights in the invention.

BACKGROUND OF THE INVENTION

During inflammation, cytokines are secreted by a myriad of cell types in response to endotoxin or other proinflammatory stimuli. Exemplary cytokines include tumor necrosis factor (TNF), interferon-gamma (IFN-γ), interleukin-1β (IL-1β) and high mobility group B-1 (HMGB-1). TNF functions as a cell-associated or secreted protein that interacts with a receptor of the TNF receptor family, which in turn communicates with the interior of the cell, with components of TNF receptor associated factors.

The cytokines are important and critical inflammatory mediators of a wide variety of disease states and conditions. For example, TNF-mediated inflammation results in tissue injury, causing a variety of cellular damage, by generating procoagulant activity on endothelial cells (Pober et al., *J. Immunol.* (1986) 136(5):1680–7), increasing the adherence of neutrophils and lymphocytes (Pober et al., *J. Immunol.* (1987) 138(10):3319–24), and stimulating the release of platelet activating factor from macrophages, neutrophils and vascular endothelial cells (Camussi et al., *J. Exp. Med.* (1987) 166(5):1390–404).

Excessive or unregulated TNF production or activity has been implicated in mediating or exacerbating rheumatoid arthritis, rheumatoid spondylitis, osteoarthritis, gouty arthritis and other arthritic conditions, sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, reperfusion injury, graft v. host rejection, allograft rejections, fever and myalgia due to infection, cachexia secondary to infection or malignancy, cachexia secondary to acquired immune deficiency syndrome (AIDS), AIDS related complex (ARC), keloid formation, scar tissue formation, Crohn's disease, ulcerative colitis and psoriasis.

For example, to expand on a specific cytokine-mediated condition, disseminated bacterial infection causes sepsis, a catastrophic clinical syndrome that develops in 750,000 people, and is associated with mortality in about 30% of those affected. (Angus et al., *Crit. Care Med.,* (2001) 29(7):1303–10.) Antibiotics can eradicate infection, but mediators released systemically by the innate immune system mediate the characteristic signs of sepsis, including microvascular hyperpermeability, coagulopathy, organ failure, tissue injury and lethal shock. (Marshall et al., *Crit. Care Med.* (2001) 29(7 Supp):S99–106.) Significant advances have been made in understanding the activities and mechanisms of specific immune-derived mediators, and the role of timing in the resultant cytokine cascade. Nonetheless, the development of effective clinical therapeutics for sepsis has been hampered by observations that previously described agents must be given prior to the development of sepsis or very soon after onset of the syndrome in order to improve survival, a scenario that is obviously difficult to apply to typical clinical situations.

The systemic inflammatory mediators of lethal sepsis have "early" and "late" components. TNF is the predominate early mediator of lethal shock and tissue injury; it is released within two hours after the onset of acute infection, and it activates the release of other proinflammatory mediators in a "cytokine cascade." High mobility group B-1 (HMGB-1), a cytosolic and nuclear protein first identified as a non-chromosomal DNA-binding protein, was recently implicated as a "late" mediator of sepsis-related lethality. HMGB-1 is released by endotoxin-stimulated macrophages, but only after a delay of 12–18 hours; a similar delay in HMGB-1 appearance is observed in the serum of mice during endotoxemia, an experimental model that induces a sepsis-like systemic cytokine response. (Wang et al., *Science* (1999) 285:248–251.) Anti-HMGB-1 antibodies confer significant protection against delayed endotoxin lethality, even when antibody dosing is initiated at a time after the early cytokine responses have peaked and resolved. (Wang et al., *Science* (1999) 285:248–251.) Other cytokine activities of HMGB-1 include stimulation of macrophages to release TNF, IL-1β, and other inflammatory products, inducing chemotaxis of smooth muscle cells, and mediating acute lung injury and lethality. (Abraham et al., *J. Exp. Med.* (2000) 165:2950–2954.)Most drug targets available today are so-called "alarm phase" cytokines, such as TNF and IL-1β, that are released early in the inflammatory response. In the clinical environment, it typically takes many hours to recognize sepsis and institute specific treatment; accordingly, it is not surprising that agents directed against these early proinflammatory cytokines have proved to be ineffective when tested in large clinical trials. (Abraham et al., *Lancet* (1998) 351(9107):929–33; Fisher et al., *JAMA* (1994) 271(23):1836–43.)

It would be useful to specifically ameliorate cytokine-mediated inflammatory conditions with a composition that inhibits, suppresses or antagonizes the production or activity of cytokines, both early and late phase mediators.

SUMMARY OF THE INVENTION

This invention is directed to a method of ameliorating deleterious cytokine effects during inflammation and other cytokine-mediated conditions. In one aspect, the invention prevents endotoxin-induced lethality by attenuating the release of "early" (tumor necrosis factor (TNF) and interleukin-1β (IL-1β)) and "late" (high mobility group B-1 (HMGB-1)) phase mediators of pathogenic systemic injuries. The method of the invention also provides for a wider treatment window than previously described.

The present invention features administering to a patient a composition comprising alpha-ketoalkanoic acid and/or one of its derivatives, which specifically includes a physiologically-acceptable salt of alpha-ketoalkanoic acid, an ester of alpha-ketoalkanoic acid, or an amide of alpha-ketoalkanoic acid for the treatment of a cytokine-mediated inflammatory condition. Suitable alpha-ketoalkanoic acids include $C_3$–$C_8$ straight chained or branched alpha-ketoalkanoic acids, for example, pyruvic acid. Physiologically acceptable salts, of alpha-ketoalkanoic acids include $Na^+$, $K^+$, $Ca^{++}$, $Mg^{++}$, $NH_4^+$ and the like.

Preferably, the therapeutic agent used in the method disclosed herein is an effective amount of an ester of an alpha-ketoalkanoic acid, for example, a $C_3$–$C_8$ straight-chained or branched alpha-ketoalkanoic acid ester. Examples include alpha-keto-butyrate, alpha-ketopentanoate, alpha-keto-3-methyl-butyrate, alpha-keto-4-methyl-pentanoate or alpha-keto-hexanoate. Pyruvate is preferred. A variety of groups are suitable for the ester position of the molecule, e.g., alkyl, aralkyl, alkoxyl, carboxyalkyl, glyceryl or dihydroxy acetone. Specific examples include ethyl, propyl, butyl, carboxymethyl, acetoxymethyl, carbethoxymethyl and ethoxymethyl. Ethyl esters are preferred. Thiolesters (e.g., wherein the thiol portion is cysteine or homocysteine) are also included.

In a preferred embodiment, the pharmaceutical composition used in the disclosed method comprises ethyl pyruvate, propyl pyruvate, carboxymethyl pyruvate, acetoxymethyl pyruvate, carbethoxymethymethyl pyruvate, ethoxymethyl pyruvate, ethyl alpha-keto-butyrate, ethyl alpha-ketopentanoate, ethyl alpha-keto-3-methyl-butyrate, ethyl alpha-keto-4-methyl-pentanoate, or ethyl alpha-keto-hexanoate. Ethyl pyruvate is more preferred.

In yet another aspect, the therapeutic agent used in the method disclosed herein is an effective amount of an amide of an alpha-ketoalkanoic acid. Suitable amides of alpha-ketoalkanoic acids for use in the method of the present inventions include compounds having the following structural formula: $RCOCONR^1R^2$. R is an alkyl group; $R^1$ and $R^2$ are independently —H, alkyl, aralkyl, alkoxyalkyl, carboxyalkyl or —$CHR^3COOH$; and $R^3$ is the side chain of a naturally occurring amino acid. Preferably, the amide of an alpha-ketoalkanoic acid is a pyruvamide.

In another aspect, when the ester derivative is used, a component for inducing and stabilizing the enol resonance form of the ester at physiological pH values is included in the composition. The stabilizing component is a cationic material, preferably a divalent cation, and most preferably calcium or magnesium. This composition further comprises a pharmceutically acceptable inert carrier substance in which the enol resonance form of the ester is stabilized at physiological pH values.

The pharmaceutically acceptable inert carrier in the composition of the invention can be any carrier substance generally recognized as safe for administering a therapeutic agent to a mammal, e.g., a buffer solution for infusion, a tablet for oral administration or in gel, micelle or liposome form for on-site delivery. Examples of delivery solutions include isotonic or hypertonic saline; bicarbonate, phosphate or citrate buffer, plasma extender, or a microcolloid or microcrystalline solution.

The conditions treatable by the method of the invention include, but are not limited to, local and systemic inflammation, inflammatory bowel disease (Crohn's disease and ulcerative colitis), rheumatoid arthritis, asthma (including status asthmaticus), sepsis and septic shock. The method of the invention also includes the treatment of inflammatory skin conditions, e.g., psoriasis and eczema.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows.

Unexpectedly, it has been discovered that a composition comprising alpha-ketoalkanoic acid and/or one of its derivatives can ameliorate a cytokine-mediated inflammatory condition. The method of the invention has been tested, e.g., in a standard mouse model of murine sepsis, in which it was shown that ethyl pyruvate rescues mammals from lethal sepsis caused by peritonitis, even when the first doses of a derivative of pyruvate were administered 24 hours after sepsis was established. The precise mechanism(s) responsible for the protective actions of pyruvate and/or its derivatives remain to be elucidated. Nevertheless, an exemplary derivative, ethyl pyruvate, is shown herein to inhibit the release of both TNF and HMGB-1 from LPS-stimulated macrophages and to down-regulate activation of the pro-inflammatory p38 MAP kinase and NF-κB signal transduction pathways. These data suggest that treatment using pyruvate and/or its derivatives in patients with established sepsis can be deferred even after the onset of clinical signs of inflammation.

In an effort to obtain some clues regarding the basis for the therapeutic benefit afforded by ethyl pyruvate in murine models of acute endotoxemia and lethal polymicrobial bacterial peritonitis, the effect of the compound on activation of two important pro-inflammatory signaling cascades was assessed. These studies revealed that the incubation of LPS-stimulated macrophages with ethyl pyruvate inhibits signal transduction through two essential pathways, p38 MAP kinase and NF-B. Macrophage activation by endotoxin, cytokines, and products of cell injury lead to the nuclear translocation of NF-B, a transcription factor that enhances the transcription of TNF and other products of the activated macrophage (Senftleben et al., Crit. Care Med. (2002) 30(1 Suppl):S18–26). Macrophage activation also leads to phosphorylation of p38 MAP kinase, a pathway that has been implicated in stabilizing TNF mRNA, and increasing TNF translation efficiency (Adams et al., Prog. Med. Chem. (2001) 38:1–60).

The late stage mediator of delayed endotoxin lethality, HMGB-1, is a cytosolic and nuclear protein known previously only as a transcription factor that stabilizes nucleosome structure. HMGB-1 is released by activated macrophages, but only after a significant lag of 12–18 hours; a similar kinetic course is observed during lethal endotoxemia (Wang et al., Science (1999) 285:248–251). This delayed kinetic of HMGB-1 release enables the application of anti-HMGB-1 antibodies downstream of the early TNF response, suggesting a therapeutic approach that can target a late mediator of lethality. The present study found that ethyl pyruvate significantly inhibited HMGB-1 release from macrophages, and decreased serum HMGB-1 levels in septic mice. Macrophages contain large quantities of HMGB-1 in the cytosol that provide a preformed pool of HMGB-1 that can be released during activation. The mechanism(s) that regulate HMGB-1 release from macrophages is enigmatic, but the present data indicate that ethyl pyruvate inhibits the release of the cytosolic protein from activated macrophages. Inhibition of HMGB-1 release by ethyl pyruvate was specific, because ethyl pyruvate did not affect intracellular HMGB-1 protein expression or stability. The present studies show that ethyl pyruvate inhibition of signaling through NF-κB and p38 MAPK pathway may underlie the ability of ethyl pyruvate to suppress HMGB-1 release from LPA-stimulated cells. Additionally, inhibition of TNF in the local macrophage milieu contributes to inhibition of HMGB-1 release, because TNF is a potent inducer of HMGB-1 release.

Together, these results reveal that pyruvate and/or its derivatives have the therapeutic potential for disease mediated by an excess of TNF-α and HMGB-1. Preferably, ethyl pyruvate is a relatively non-toxic food additive, and the observed effects occur in therapeutically achievable and safe levels. Ethyl pyruvate can be administered in Ringer's-type crystalloid fluid, a calcium- and potassium-containing balanced salt solution that is widely used as resuscitating agent for the treatment of shock.

Accordingly, it is a primary object of this invention to provide new method of treating inflammatory conditions, particularly those that are mediated by cytokines, using an improved composition containing alpha-ketoalkanoic acid and/or its derivatives.

Figure 1A:
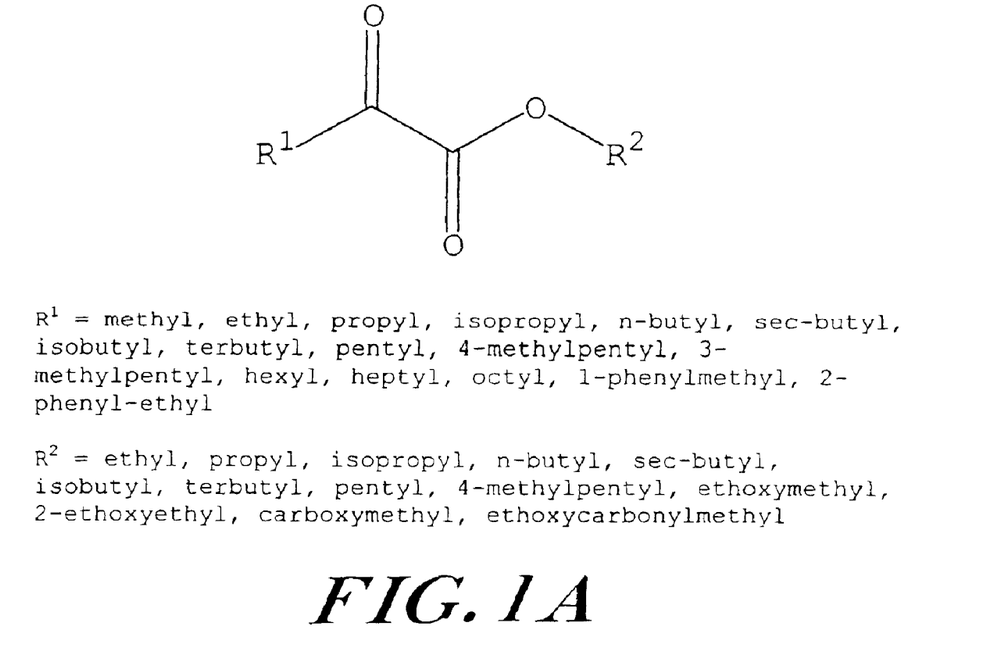
FIGS. 1A–B show the structures of the preferred alpha-ketoalkanoic acid esters and amides in the composition of the invention.
Figure 1B:
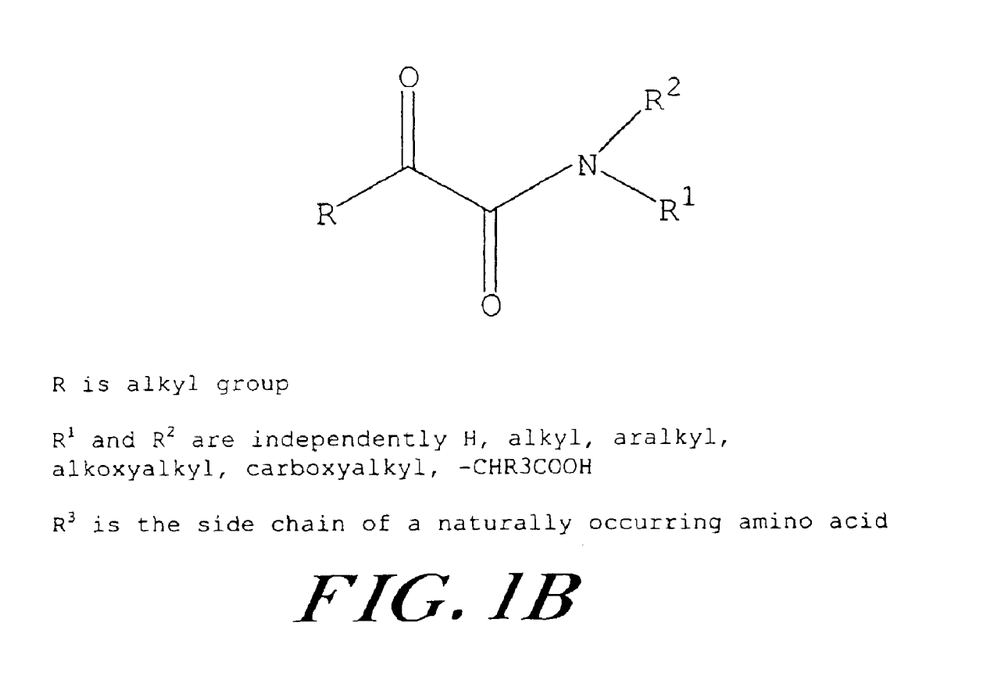

To achieve the foregoing object and in accordance with the purpose of the invention, as embodied and broadly described herein, one composition of this invention comprises a alpha-ketoalkanoic acid ester, in accordance with the molecular structures shown in FIG. 1, admixed with a sufficient concentration of biologically safe organic or inorganic cations to induce enolization of the alpha-keto functionality of the ester at physiological pH values. In a preferred embodiment, the composition comprises an alkyl ester of alpha-ketopropionic acid (pyruvic acid), the ester is the ethyl analog and the cation is a divalent cation, particularly either calcium or magnesium. In a particularly preferred formulation of the composition of the invention, the ester compound is ethyl pyruvate admixed with calcium ion in a Ringer's solution at a pH of about 7–8.

The therapeutic compositions of the invention may be administered orally, topically (e.g., ointment, gel or cream), or parenterally, (e.g., intranasally, subcutaneously, intramuscularly, intravenously, intraluminally, intra-arterially, intravaginally, transurethrally or rectally) by routine methods in pharmaceutically acceptable inert carrier substances. For example, the therapeutic compositions of the invention may be administered in a sustained release formulation using a biodegradable biocompatible polymer, or by on-site delivery using micelles, gels, liposomes, or a buffer solution.

Preferably, the pharmaceutical composition is administered as an infusate at a concentration of, e.g., 10 mM to 200 mM, preferably 20 mM to 90 mM of alpha-ketoalkanoic acid, at a rate of 1 mg/kg body weight/day to 200 mg/kg body weight/day, in a buffer solution as described herein. More preferably, the pharmaceutical composition is administered as an infusate at a concentration of about 28 mM of alpha-ketoalkanoic acid, at a dose of 100 mg/kg body weight/day to 150 mg/kg body weight/day of alpha-ketoalkanoic acid, in a buffer solution. In bolus form, the active agent can be administered at a similar dosage, e.g., 1 mg/kg body weight/day to 200 mg/kg body weight/day of alpha-ketoalkanoic acid, where the dosage is divided into aliquots and delivered 1 to 4 times daily (for a total dosage of 1 mg/kg body weight/day to 200 mg/kg body weight/day), with the concentration of alpha-ketoalkanoic acid adjusted accordingly. The enolization agent in the composition of the invention is at an appropriate concentration to induce enolization of the alpha-keto functionality of the amount of active ester agent in the administered composition. Optimal dosage and modes of administration can readily be determined by conventional protocols.

Exemplary cytokine-mediated inflammatory conditions include, but are not limited to, local and systemic inflammation, inflammatory bowel disease (Crohn's disease and ulcerative colitis), rheumatoid arthritis, asthma (including status asthmaticus), endotoxemia, sepsis and septic shock, also including inflammatory skin conditions, for example, psoriasis and eczema.

The following examples are presented to illustrate the advantages of the present invention and to assist one of ordinary skill in making and using the same. These examples are not intended in any way otherwise to limit the scope of the disclosure.

Exemplary Materials and Methods

Animal Experiments. Male 6–8 week old Balb/C mice (20–25 g) were purchased from Harlen Sprague-Dawley (Indianapolis, Ind.) and allowed to acclimate for 7 days housed at 25° C. on a 12 h light/dark cycle. Animals were randomly grouped (10 mice per group) and assigned to a specific experiment. All animal experiments were performed in accordance with the National Institutes of Health Guidelines under protocols approved by the Institutional Animal Care and Use Committee of North Shore University Hospital and New York University Medical School.

Endotoxin shock. Mice were injected with endotoxin (*Escherichia coli* lipopolysaccharide, LPS 0111:B4; Sigma Chemical Co, St. Louis, Mo.) that was dissolved in sterile pyrogen-free saline at stock concentrations of 10 mg/ml. LPS solutions were sonicated for 20 min immediately prior to use for each experiment. Mice received an $LD_{75}$ dose of LPS (5 mg/kg, i.p.). Blood was collected at different times after LPS administration, allowed to clot for 2 h at room temperature, then centrifuged for 20 min at 1,500 g. Serum samples were stored at 20° C. prior to analysis. Mortality was recorded for up to 3 weeks after injection to ensure that no additional late deaths occurred.

Cecal ligation and puncture (CLP). Cecal ligation and puncture (CLP) was performed as described by (Wichterman et al., *J. Surg. Res.* (1980) 29(2):189–201). Briefly, mice were anesthetized with 20 mg/ml xylazine intramuscularly at a dose of 1.0 g/kg, a midline incision was performed, and the cecum was isolated. A 6-0 prolene suture ligature was placed at a level 5.0 mm from the cecal tip away from the ileocecal valve. The ligated cecal stump was then punctured once with a 22-gauge needle, and stool extruded (1 mm) to ascertain patency of the puncture site. The cecum was then placed back into its normal intra-abdominal position, and the abdomen was closed with a running suture of 6-0 prolene in two layers, peritoneum and fascia separately, to prevent leakage of fluid. All animals received an antibiotic (primexin 0.5 mg/kg s/c) 12 hr after surgery as a single dose. All animals received resuscitation with normal saline 24 hr after surgery as a single injectate (20 ml/kg of body weight). Mortality was recorded for up to 1 week after the procedure; survivors were followed for 3 weeks to ensure no late mortalities had occurred.

Ethyl Pyruvate Solution: Ethyl pyruvate was prepared in solution with sodium (130 mM), potassium (4 mM), calcium (2.7 mM), chloride (130 mM), and ethyl pyruvate (28 mM); pH 7.0). For injections in mice solutions were diluted so that each injection volume was 0.4 ml per dose.

Cell Culture. BALB/c murine macrophage-like RAW 264.7 cells obtained from the American Type Culture Collection (ATCC Number TIB-71, ATCC, Rockville, Mass.) (61), were cultured in RPMI 1640 (Life Technologies, Grand Island, N.Y.) supplemented with 10% heat inactivated fetal bovine serum (Gemini, Calabasas, Calif.), 2 mM glutamine (Cat. # 25030-149, Gibco BRL, Rockville, Mass.) and antibiotic-antimycotic mix (Cat. # 15240-062, Gibco BRL, Rockville, Mass.) in a humidified incubator with 5% $CO_2$. Cells were mechanically removed and resuspended in serum-free Opti-MEM I medium (Life Technology, Grand Island, N.Y.) to perform experiments at 75% confluence.

Cytokine measurements. TNF concentration in mouse serum and in conditioned media from RAW 264.7 cell cultures was measured by ELISA (minimum detectable concentration=10 pg/ml). Recombinant mouse TNF standards were obtained from R&D Systems (Inc., Minneapolis, Minn.) and dissolved in 0.1% bovine serum albumin solution (BSA, low endotoxin grade from Sigma Chemical Co., St. Louis, Mo.). Monoclonal antibody to mouse TNF was purchased from Biosource International, Inc., Camarillo, Calif. Human TNF monoclonal antibody, human TNF antiserum and mouse TNF antiserum were prepared and contributed by Dr. Christine Metz. Mouse serum IL-6 and IL-1β levels were measured using ELISA kits (R&D Systems, Inc., Minneapolis, Minn.). HMGB-1 was analyzed by western blot as previously described by Wang et al, 1999. Briefly, serum or cell culture conditioned media was first filtrated through centricon YM-100 (Millipore Corp., Bedford, Mass.) to clear the samples from cell debris and macromolecular complex formed during clotting. Then, samples were concentrated 15 folds by using centricon YM-30 and subjected to 12% SDS-polyacrylamide gels (SDS-PAGE). Protein was electroblotting to Immun-blot PVDF membrane (Bio-rad, Hercules Calif.) and HMGB-1 was analyzed using polyclonal 241 antibody and secondary anti-rabbit horseradish peroxidase (Amersham, Pitscataway, N.J.). Standard curves were constructed using r-HMGB-1, and the intensity of the 30 kD band analyzed by densitometry.

Nuclear extract preparation. The day before use, cells were plated at a density of $1\times10^6$ per well in 6 well tissue culture plates. After stimulation at indicated times, cells were removed from the incubator and place on ice immediately. Cells were washed once with 2 ml phosphate buffered saline (PBS) then harvested in 1 ml of PBS containing 2% FBS using rubber scrapper. The cells were transferred to a 1.5 ml tube and centrifuged at 14,000 g for 10 s; the pellet was resuspended in 600 µL of buffer I (10 mM pH=7.8 Tris.HCL, 10 mM KCL, 1.5 mM $MgCl_2$, 0.3M sucrose, 500 µM phenylmethylsulfonyl fluoride, 1.0 mM sodium orthovanadate, 1 mM dithiothreitol, and protease inhibitor cocktail (Sigma-Aldrich Catalog # p-8340) and incubated for 15 min. 38.3 µl 10% NP40 was added and the tube was vortexed at full speed for 10 s. Nuclei were isolated by centrifugation at 300 g for 3 min. The supernatant was aspirated, and the nuclear pellet was gently resuspended in 80 µL of buffer II (10 mM pH=7.8 Tris. HCL, 420 mM KCL, 1.5 mM $MgCL_2$, 20% glycerol). Following a 15 min incubation, nuclear extracts were cleared by centrifugation at 14,000 g for 10 min. The supernatant was transferred to a new tube, protein concentration was determined using a commercially available Bradford assay (Bio-Rad Protein Assay, Hercules, Calif.). Nuclear extracts were frozen at −80° C.

Electrophoretic Mobility Shift Assays (EMSA). The sequence of the double-stranded NF-κB oligonucleotide was as follows: Sense: 5'-AGT TGA GGG GAC TTT CCC AGG C-3' (SEQ ID NO: 1), antisense: 3'-TCA ACT CCC CTG AAA GGG TCC G-5' (SEQ ID NO: 2) (Promega, Catalog # E3291). The oligonucleotides were end-labeled with $^{\gamma-32}P$ adenosine triphosphate (New England Nuclear, Boston, Mass.) using T4 polynucleotide kinase (Promega, Madison, Wis.). 3 µg of nuclear protein/reaction was incubated with $^{\gamma-32}P$-labeled NF-κB probe in bandshift buffer (13 mM pH=8.0 HEPES, 65 mM NaCl, 1 mM DTT, 0.14 mM EDTA, 8% glycerol) in the presence of 1 ng of calf thymus DNA for 20 min at room temperature. For competition reactions 100 fold molar excess of cold oligonucleotide was added simultaneously with labeled probe. Supershift assays were performed by incubating nuclear extracts with 2 µL of anti-p65 and anti-p50 (Santa Cruz Biotechnology) for 1 h prior to the addition of radiolabeled probe. The binding reaction mixture was electrophoresed on 4% nondenaturing polyacrylamide electrophoresis (PAGE) gels. After PAGE, the gels were dried and exposed to XAR-5 film (Kodak, Rochester, N.Y.) at −80° C. overnight using an intensifying screen.

Total RNA extraction and RNase protection assay. Total RNA was extracted from cultured cells by using RNAzol B in accordance with the manufacturer's instructions (Tel-Test "B" Inc, Friendswood, Tex.). The integrity of the RNA was verified by electrophoresis on 1.2% agarose/17% formaldehyde gels. The levels of TNF and cyclophilin mRNA in RAW cells were measured using an RNase protection assay kit from PharMingen in accordance with the manufacturer's instructions (San Diego, Calif.). The antisense RNA probe was labeled with $^{\alpha-32}P$-UTP (800 Ci/mmol, Amersham, Ill.) using T7 RNA polymerase. The protected transcript of TNF is 287 bp, and the control transcript (cyclophilin) is 105 bp. Molecular weight markers were prepared using pBR-322 plasmid DNA digested with MSP I (New England Bio Labs, Beverly, Mass.) and Klenow end-labeled (Strategene, La Jolla, Calif.) with $^{\alpha-32}P$-dCTP (800 Ci/mmol, Amersham); mRNA levels were measured with an InstantImager (Packard Instrument Co., Meriden, Conn.).

Statistical analysis. All data in the figures and text are expressed as mean±SEM for at least 20 animals per condition. Significance of Differences between groups were determined by two-tailed Student's t-test, one way ANOVA followed by the least significant difference test or Fisher's LSD Exact Test or the Chi-square test, as appropriate. FD4 clearance data were logarithmically transformed prior to performing statistical analyses. Differences were considered significant for $p<0.05$.

EXAMPLE I

Stability of Pyruvate Esters in Solution

Ethyl pyruvate affords a more stable aqueous solution than sodium pyruvate in the presence of calcium salts, and this observation can be extended to the study of other pyruvate ester analogs, as shown in FIG. 1A, by dissolving them in Ringer's solution containing at least 0.2 equivalents of calcium per molar equivalent of pyruvate analog titrated with sodium hydroxide, or other suitable inorganic alkali, to physiological pH values. A specific "pyruvated" Ringer's solution for use in NMR, stability, and subsequent biological studies is shown in Table 1. Another exemplary buffer solution is given in Table 2.

It is to be understood that the pyruvate analog in the instant example may be substituted with any of the analogs shown in FIG. 1 at any concentration sufficient to afford a homogenous solution or substituted by control substances for comparative purposes, such as pyruvic acid, lactic acid (as would be the case in "lactated" Ringer's solution and other reference or inactive ketoacid analogs. The calcium cation may also be substituted, e.g., with magnesium or any other biologically safe cation capable of substituting for calcium and stabilizing the formation of transient coordination complexes with pyruvate ester enolates in aqueous solution.

TABLE 1

Constituents of a Ringer's Ethyl Pyruvate Solution (REPS)

| Component | Composition | Range |
|---|---|---|
| Isotonic saline | 75 cc | — (fixed) |
| KCl | 11.25 | — (fixed) |
| $CaCl_2$ | 7.5 mg | 5–20 mg |
| Ethyl pyruvate | 0.781 ml | 0.5–1.5 ml |
| NaOH | To pH 7.5 | 7.35–7.55 (pH) |

TABLE 2

Constituents of a Citrate Ethyl Pyruvate Solution

| Component | Composition |
|---|---|
| Isotonic saline (NaCl) | 102 mM |
| KCl | 4 mM |
| $CaCl_2$ | 2.7 mM |
| Ethyl pyruvate | 10 mg/ml |
| Sodium citrate | 200 mM |

(Adjusted to pH 4–5.)

EXAMPLE II

Ethyl Pyruvate Effect Against Inflammation in an in Vitro Model of Intestinal Epithelial Injury To test for the effect of ethyl pyruvate on a stabilizing calcium salt solution (REPS) in a cytokine-induced intestinal epithelial hyperpermeability condition, an in vitro model of intestinal epithelial injury due to inflammation, such as might occur in cases of inflammatory bowel disease (i.e., Crohn's disease or ulcerative colitis) was used.

Exemplary materials and methods include the following, while minor modifications can be made: Caco-2 human enterocytes ($10^5$ cells/well) were plated on permeable filters in 12-well Transwell bicameral chambers (COSTAR, Corning, N.Y.) and fed biweekly. Permeability studies were carried out using confluent monolayers between 21–28 d after seeding. The permeability probe was FITC-labeled dextran (4400 Da; FD4). A sterile stock solution of FD4 (25 mg/ml) was prepared by dissolving the compound in HEPES-buffered DMEM complete medium (pH 6.8) and passing it through a filter (0.45 m pore size). For permeability studies, the medium was aspirated from the apical and basolateral sides of the Transwell chambers. FD4 solution (200 µl) was added to the apical compartments. The medium on the basolateral side of the Transwell chambers was replaced with 500 µl of control medium or medium containing cytomix (1 ng/ml IL-1β+10 ng/ml TNF-α+1000 U/ml IFN-γ), or medium with cytomix and graded concentrations of ethyl pyruvate. After 24 and 48 h of incubation, 30 µl of medium was aspirated from the basolateral compartments for spectrofluorometric determination of FD4 concentration as previously described. (Menconi et al., *Am. J. Physiol.* (1997) 272:G1007–G1021.) The permeability of monolayers was expressed as a clearance (C), which was calculated as previously described. (Menconi et al., *Am. J. Physiol.* (1997) 272:G1007–G1021.) Results at 48 h are depicted in the figure (* indicates P<0.01 versus cytomix alone).

Figure 2:
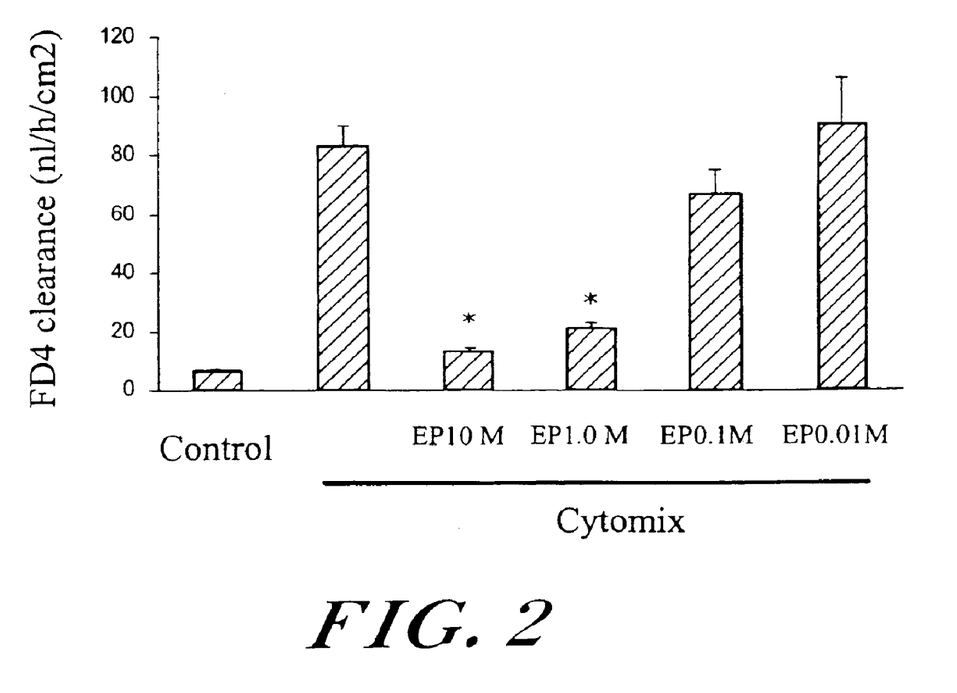
FIG. 2 depicts a bar graph showing the effect of ethyl pyruvate on the permeability of Caco-2 monolayers incubated for 48 hours with a cocktail of cytokines ("cytomix") ("Cyto") containing IFN-γ (1000 U/ml), IL-1β (1 nM) and TNF-α (10 ng/ml). REPS blocks cytokine-induced intestinal epithelial hyperpermeability.

As shown in FIG. 2, both of the highest concentrations of ethyl pyruvate significantly decreased cytomix-induced hyperpermeability (P<0.001). Ethyl pyruvate prevents the increase in permeability, which is observed when human Caco-2 enterocytic monolayers are incubated with a cocktail of pro-inflammatory cytokines.

EXAMPLE III

Figure 3A:
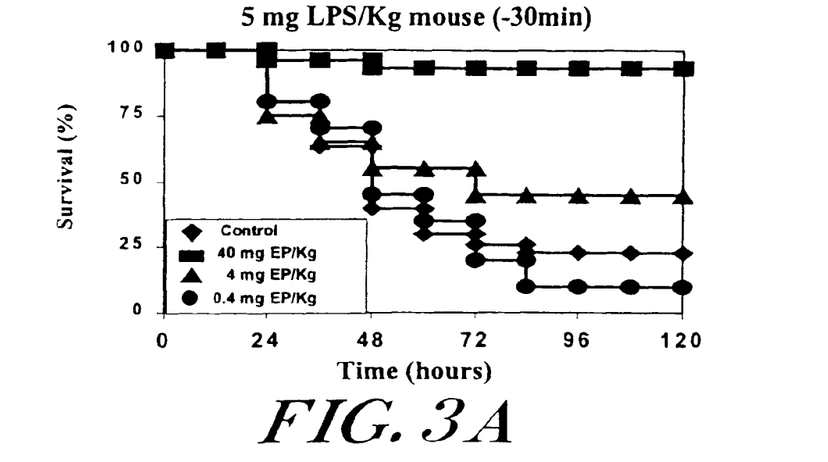
FIGS. 3A–C depict the effect of ethyl pyruvate pretreatment in preventing endotoxin lethality by attenuating TNF and HMGB-1 release in vivo. (a) Kaplan-Meier plot mice exposed to lethal doses of endotoxin (5 mg LPS/kg, i.p. at time=0 hr) after pretreatment with EP (single EP dose of 40 mg/kg; i.p. at t=−30 minutes). EP conferred significant protection against lethality ($P<0.05$). (b) Ethyl pyruvate pretreatment significantly attenuates the release of serum TNF at 2 hours after LPS. (c) Ethyl pyruvate significantly inhibits serum HMGB-1 levels at 20 hr after LPS. $P<0.05$ for TNF and HMGB-1 of EP as compared to vehicle treated endotoxemic animals; n=5 for an experiment that was repeated twice.
Figure 3B:
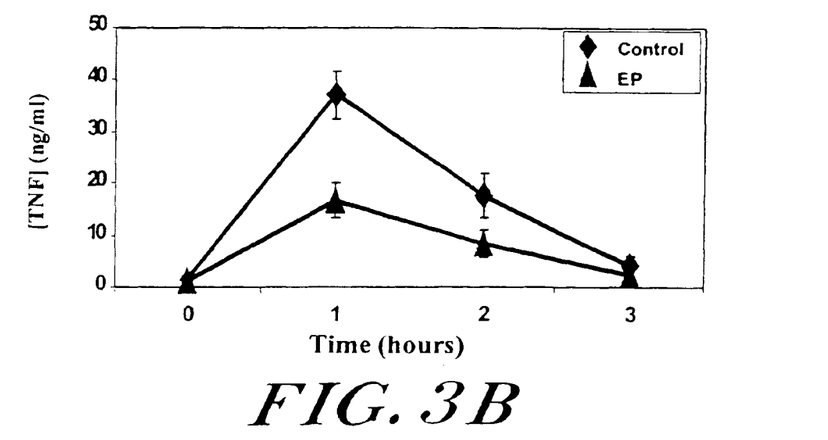
Figure 3C:
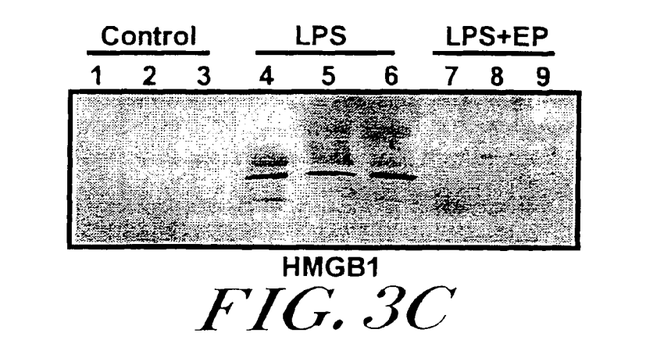

Ethyl Pyruvate Pretreatment Prevents Endotoxin Lethality by Attenuating TNF and HMGB1 Release in Vivo The initial evaluation of ethyl pyruvate (EP) was conducted as a therapeutic solution in lethal systemic inflammation in a standard model of murine endotoxemia. Balb/c mice received a single dose of ethyl pyruvate (40 mg ethyl pyruvate/kg mouse) 30 minutes before the onset of lethal endotoxemia (*E. coli* lipopolysaccharide, LPS, 5 mg LPS/kg, i.p.). Ethyl pyruvate pretreatment protected BALB/c mice from lethal endotoxemia (ethyl pyruvate survival=20/20 versus vehicle control survival=3/20; P<0.005) (FIG. 3A). Ethyl pyruvate pretreatment significantly prevented the clinical manifestations of endotoxin morbidity, including lethargy, diarrhea, piloerection, huddling, and depressed spontaneous mobility. Late deaths in ethyl pyruvate-treated animals did not occur during a subsequent 3 week period of observation, indicating that ethyl pyruvate confers a complete and lasting protection against lethal endotoxemia, and does not merely delay the onset of lethal pathology. Pretreatment of endotoxemic mice with ethyl pyruvate significantly attenuated the serum levels of both TNF (vehicle treated=17+/-4 ng TNF/ml versus ethyl pyruvate treated=39+-6 ng TNF/ml; P<0.05 (FIG. 3B) and serum HMGB1 measured 20 hours after the onset of endotoxemia (FIG. 3C). Ethyl pyruvate also attenuated the peak serum levels of IL-1 and IL6 (data not shown), indicating that ethyl pyruvate prevents endotoxin lethality by attenuating the release of early (TNF) and late (HMGB-1) mediators of lethality.

EXAMPLE IV

Figure 4A:
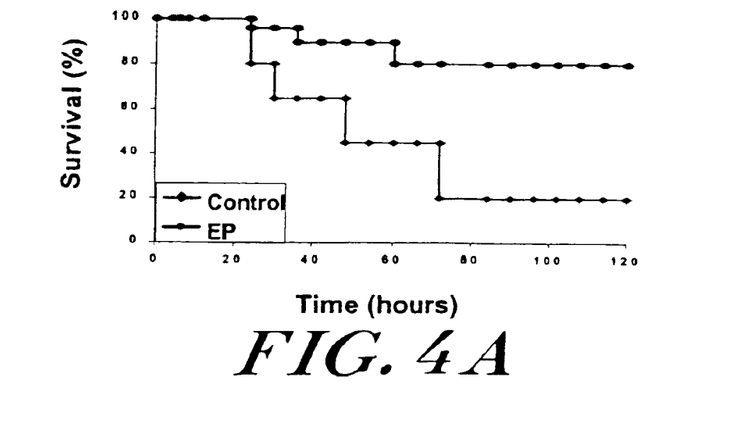
FIGS. 4A–C depict the effects of delayed administration of ethyl pyruvate in attenuating the lethality of endotoxemia and sepsis HMGB-1. (a) Kaplan-Meier plot of mice subjected to a lethal dose of LPS (3.75 mg LPS/kg; i.p.) and delayed administration of ethyl pyruvate (40 mg/kg, i.p.), starting 4 hours after LPS injection and repeatedly dosed at 8, 12, 24 and 30 h. (b) HMGB-1 release was analyzed by western blot of serum collected at 20 hrs. LPS induces the release of HMGB-1 in vivo (lanes 4, 5, 6), and delayed treatment with ethyl pyruvate (lanes 7, 8, 9) significantly prevents the release of serum HMGB-1. (c) Kaplan-Meier plot of septic mice with cecal perforation treated with ethyl pyruvate (40 mg/kg, i.p.) beginning 24 hours after the onset of peritonitis induced by cecal perforation at time=0 hr. Note that in both endotoxemia and CLP models, delayed administration of ethyl pyruvate significantly increased survival.
Figure 4B:
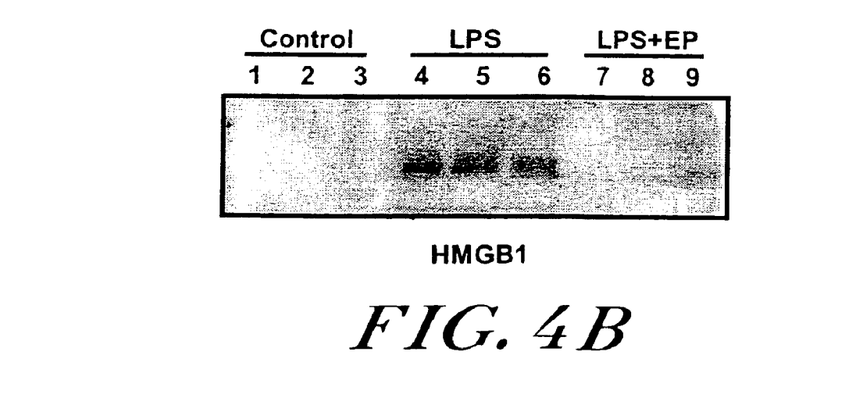

Delayed Administration of Ethyl Pyruvate Prevents the Lethality of Endotoxemia by Inhibiting HMGB1 Release The therapeutic efficacy of the delayed administration of ethyl pyruvate after the onset of endotoxemia was assessed. Ethyl pyruvate dosing in endotoxemic mice was initiated 4 hours after the onset of endotoxemia, when clinical signs were already evident, including diarrhea, piloerection, and depressed spontaneous activity (FIG. 4A). Notably, this first dose was administered after the early peak in serum TNF, which occurs within the first 1–2 hours after the onset of endotoxemia. In this delayed treatment protocol (40 mg ethyl pyruvate/kg, i.p., at 4, 8, 12, 24 and 30 hours after LPS), ethyl pyruvate significantly increased survival as compared to treatment with vehicle (vehicle survival=5/20; ethyl pyruvate survival=17/20; P<0.005). In agreement with the role of HMGB-1 as a mediator of delayed endotoxin lethality, delayed treatment of endotoxemic mice with ethyl pyruvate beginning 4 hours post-LPS injection significantly attenuated the systemic release of HMGB-1 measured at 20 hours after the onset of endotoxemia (FIG. 4B). Ethyl pyruvate treatment reversed clinical signs of morbidity, and no late deaths occurred during the 3 week period of observation, indicating that delayed treatment with ethyl pyruvate confers significant protection against lethal endotoxemia.

EXAMPLE V

Delayed Administration of Ethyl Pyruvate Prevents the Lethality of Sepsis

Figure 4C:
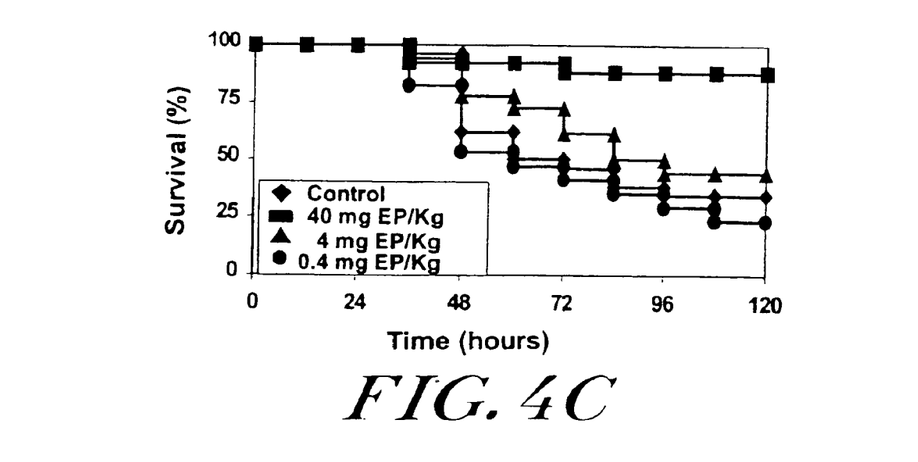

The efficacy of ethyl pyruvate as treatment for lethal sepsis in a standardized model of peritonitis caused by surgical perforation of the cecum was tested. Mice subjected to peritonitis received ethyl pyruvate (40 mg ethyl pyruvate/kg, i.p.) beginning 24 hours after the onset of peritonitis, a time at which 10% of the mice in each group had already died. Survival in vehicle-treated controls during the ensuing three weeks of monitoring was 5/17; in contrast, ethyl pyruvate treatment significantly improved survival of septic mice, resulting in survival of 14/17; P<0.005. The protection against lethal sepsis was ethyl pyruvate dose-dependent, because lower ethyl pyruvate doses failed to confer significant protection against death (FIG. 4C). To our knowledge there have not been any other experimental therapeutic agents reported to rescue septic mice when applied after 24 hours of established sepsis.

EXAMPLE VI

Ethyl Pyruvate Inhibits the Synthesis of TNF in Macrophage Cultures

Figure 5A:
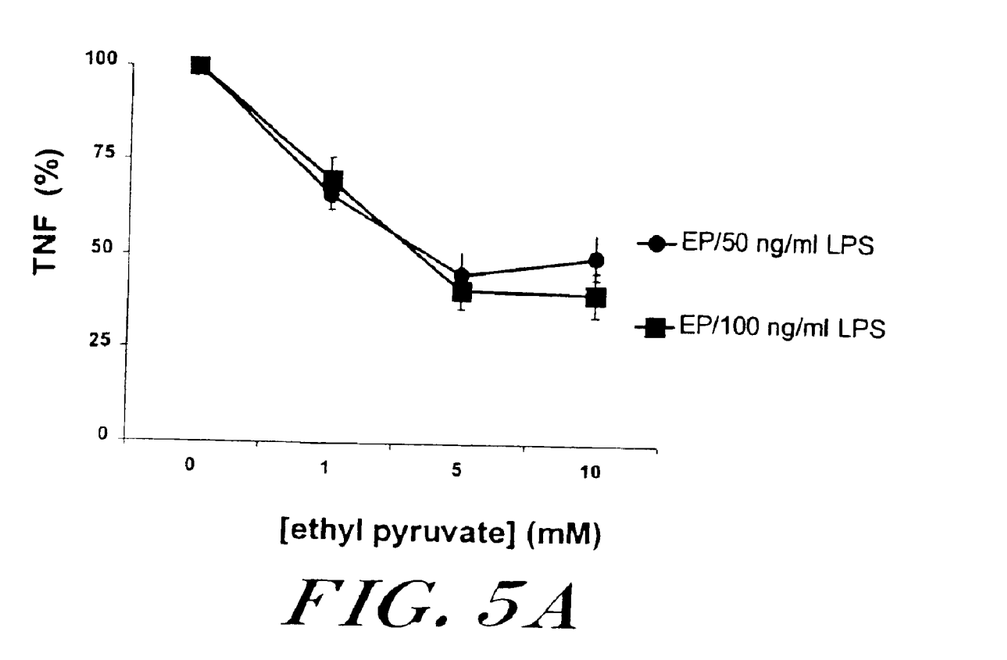
FIGS. 5A–B show that ethyl pyruvate inhibits TNF transcription and synthesis. (a) The influence of ethyl pyruvate on TNF release by LPS-stimulated macrophage cultures was measured by ELISA on macrophage conditioned media stimulated with 50 or 100 ng/ml of LPS. Note that the concentration of ethyl pyruvate that inhibited 50% of the TNF response (ethyl pyruvate $EC_{50}$) from macrophage cultures was 3.4 mM, a clinically achievable concentration. (b) Ethyl pyruvate prevents the transcription of the TNF gene. The effect of ethyl pyruvate on TNF transcription was analyzed by Ribonuclease protection assay (RPA III™, Ambion, Austin, Tex.). Note that ethyl pyruvate prevents LPS-induced transcription of TNF in an ethyl pyruvate concentration dependent fashion.
Figure 5B:
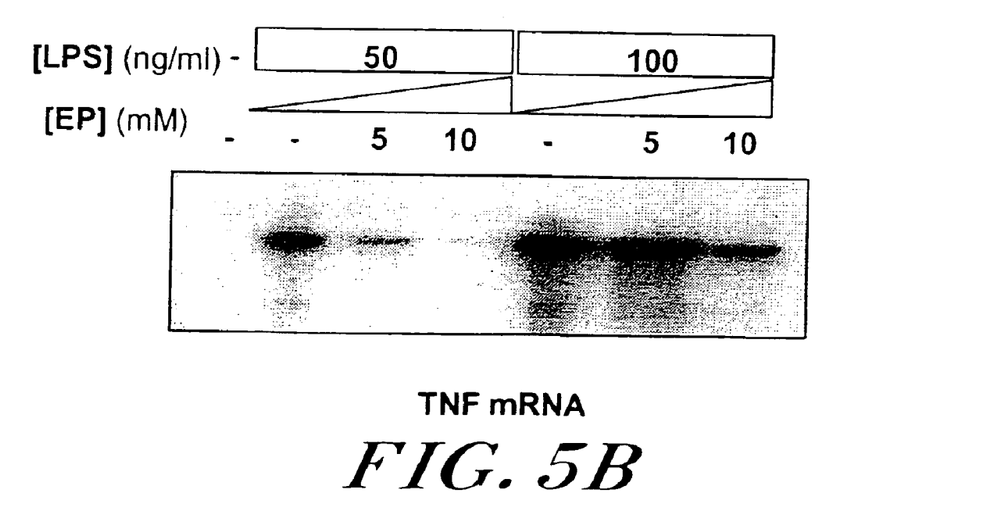

To determine the effect of ethyl pyruvate on TNF synthesis by macrophages, murine macrophage-like RAW 264.7 cells were stimulated with endotoxin, and TNF measured in the conditioned media. Ethyl pyruvate significantly inhibited TNF release in macrophage cultures (FIG. 5A). The concentration of ethyl pyruvate that suppressed 50% of the TNF response was 3.4 mM, a clinically achievable concentration. At the highest doses of ethyl pyruvate tested, the synthesis of TNF was not completely inhibited, indicating that even in the presence of saturating amounts of this agent, macrophages can still produce some level of TNF. Ethyl pyruvate inhibition of TNF in macrophages also significantly reduced the amount of TNF mRNA (FIG. 5B), indicating that ethyl pyruvate acts to suppress the steady-state levels of the TNF gene transcript in activated macrophages.

EXAMPLE VII

Ethyl Pyruvate Inhibits Signal Transduction via NF-B and p38 MAP Kinase

Figure 6A:
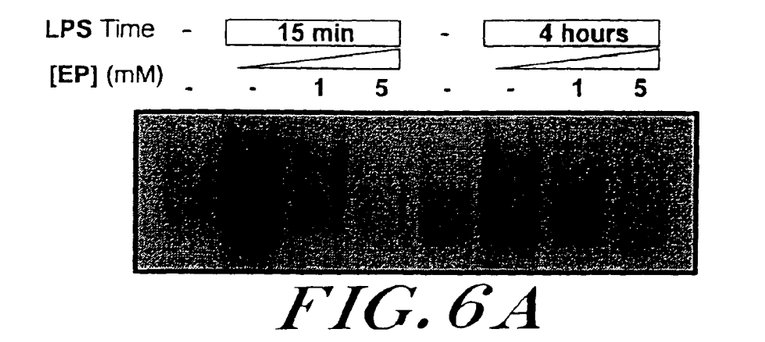
FIGS. 6A–D show that ethyl pyruvate prevents LPS-induced activation of NF-B and p38MAPK pathways in macrophage cultures. (a) RAW264.7 cells were stimulated with LPS in the presence of the indicated concentrations of ethyl pyruvate. The activation of NF-kB was analyzed by EMSA at 15 min and 4 hours using a $^{32}P$-labeled NF-B probe. Ethyl pyruvate suppressed activation of NF-B in an ethyl pyruvate concentration dependent fashion. The experiment was repeated 3 times. (b) Supershift and competition studies. Nuclear extract of macrophages stimulated with LPS and incubated with antibody against p65-Rel to induce specific supershift of NF-κB complex. Nuclear extracts were incubated with 100-fold molar excess of unlabeled (cold) NP-κB or HIF-1 probe for competition analysis. (c) RAW264.7 cells were stimulated with LPS in the presence of the indicated concentration of ethyl pyruvate. The phosphorylation of p38MAPK was analyzed by western blot using antibodies against phosphorylated (thr180/tyr182) p38MAPK (in accordance with the manufacturer (New England Biolabs, Inc Cat. # 9210, Beverly, Mass.). (d) The total amount of p38 MAPK is visualized by western blot. Ethyl pyruvate prevents the phosphorylation of p38MAPK in macrophage cultures without affecting the intracellular level of total p38MAPK.
Figure 6B:
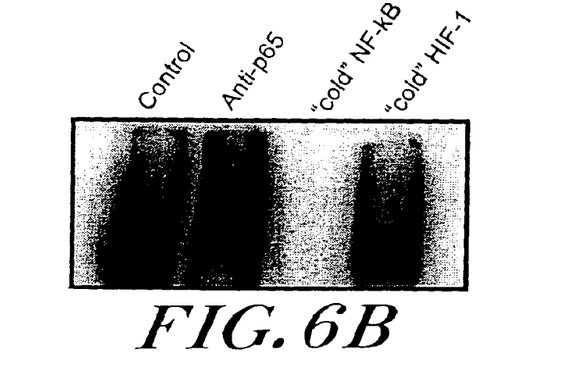
Figure 6C:
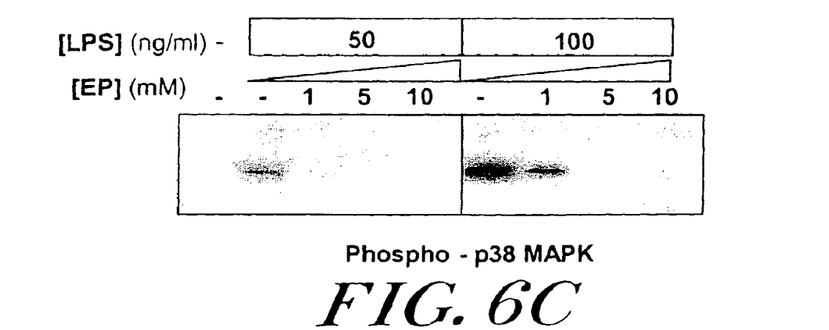
Figure 6D:
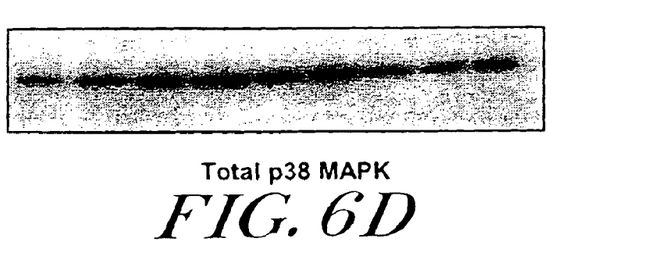

Signal transduction through NF-B and p38 MAPK pathways is a critical step in macrophage activation that leads to increased expression of TNF and other proinflammatory cytokine genes. The suppression of TNF mRNA suggested the possibility that ethyl pyruvate might inhibit the nuclear translocation of NF-B, because this transcription factor is a predominate regulator of TNF gene transcription. In agreement with previous studies, LPS induced a significant activation of NF-B as showed by EMSA at 15 minutes and at 4 hours after LPS exposure (FIG. 6A). Ethyl pyruvate significantly prevented LPS-induced activation of NF-B signaling in a concentration dependent fashion (FIG. 6A). Ethyl pyruvate inhibition of NF-B activation persisted for at least 4 hours after LPS exposure, indicating that inhibition is complete, and does merely represent a delay of pathway activation. The specificity of the ethyl pyruvate effect on NF-B was established by additional supershift and competition assays (FIG. 6B), in which anti-p65 antibodies induced a supershift in the electrophoretic mobility of the complex consistent with the presence of Rel p65 in the complex. Pretreatment of nuclear extracts with a 100-fold molar excess of unlabeled (cold) NF-B, but not unlabeled HIF1, prevented the electrophoretic shift of the radioactive probe. Ethyl pyruvate also prevented the LPS-induced phosphorylation and subsequent activation of p38 MAPK in an ethyl pyruvate concentration dependent fashion (FIG. 6C). To determine specificity of inhibiting the activation of p38 MAPK by ethyl pyruvate, the intracellular stability and concentration of total p38MAPK was assessed, and observed that ethyl pyruvate did not significantly influence the total levels of p38 MAPK (FIG. 6D). Together, these results indicate that ethyl pyruvate interferes with the activation of macrophages by suppressing signal transduction through these critical pathways.

EXAMPLE VIII

Ethyl Pyruvate Attenuates the Release of HMGB-1

Figure 7A:
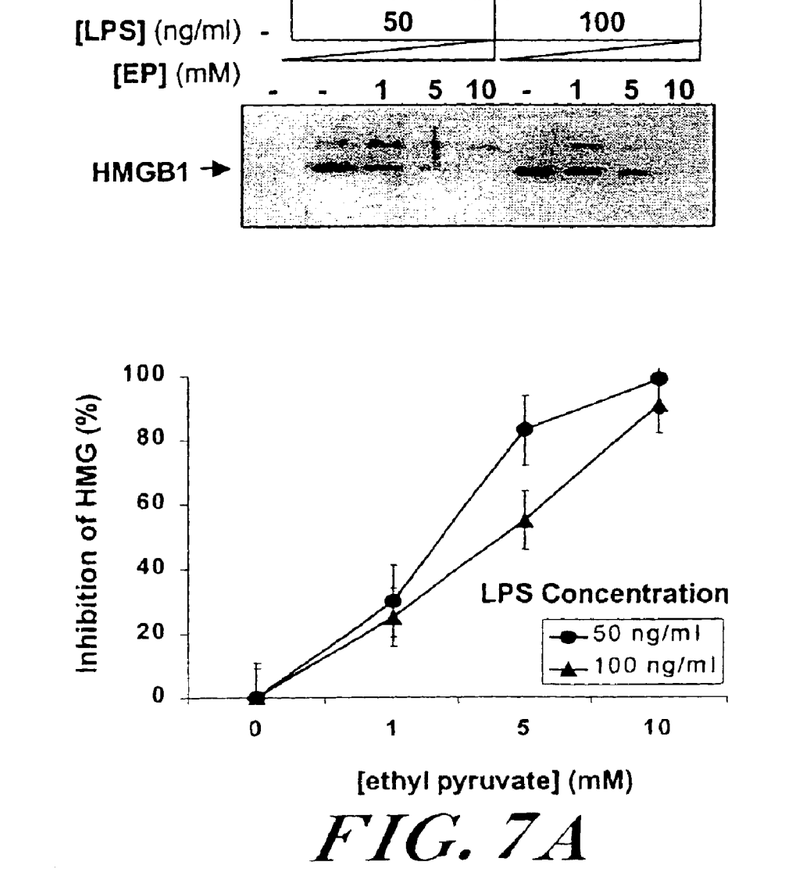
FIGS. 7A–B show that ethyl pyruvate inhibits HMGB-1 release. (a) Ethyl pyruvate inhibits release of HMGB-1 from macrophage cultures as evidenced by western blot of conditioned culture media 24 hrs after addition of LPS. (b) Analysis of the effect of ethyl pyruvate on total cell associated levels of HMGB-1. Note that ethyl pyruvate did not affect the intracellular stability and levels of HMGB-1 either at 10 or 20 h after treatment, suggesting that ethyl pyruvate specifically prevents the release of HMGB-1.
Figure 7B:
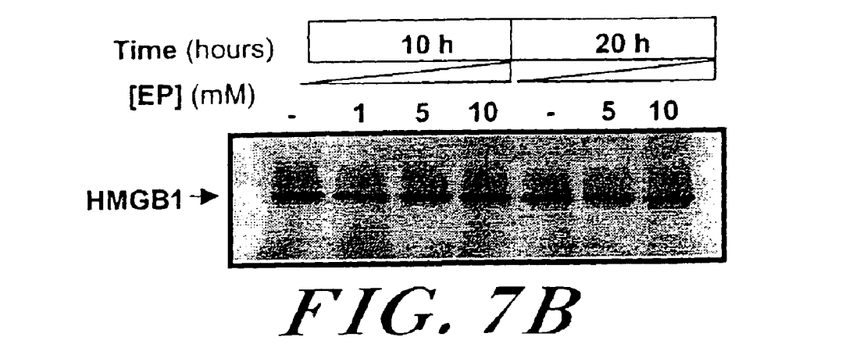

To determine whether ethyl pyruvate directly inhibits HMGB-1 release from macrophages, HMGB-1 release was measured in media conditioned by overnight endotoxin-exposed macrophage cultures. Ethyl pyruvate significantly prevented LPS-induced HMGB-1 release in a concentration dependent manner (FIG. 7A). Most of the HMGB-1 released by activated macrophages exists as a preformed cell associated protein, so to distinguish between the possibilities that ethyl pyruvate either inhibited the release of HMGB 1 or else suppressed the total cellular levels of HMGB-1, total cell associated HMGB1-levels in macrophages was measured. RAW264.7 cells were treated with 1, 5 or 10 mM of ethyl pyruvate, and total cell associated HMGB-1 protein levels analyzed (FIG. 7B). Ethyl pyruvate did not significantly influence total intracellular HMGB1 protein concentration indicating that ethyl pyruvate specifically prevented HMGB1 release without affecting protein synthesis or stability.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for treating a cytokine-mediated inflammatory condition in a patient suffering therefrom, comprising:
   administering to said patient an effective amount of a composition comprising an ester of an alpha-ketoalkanoic acid selected from the group consisting of alpha-ketopropionic acid (pyruvate), alpha-keto-butyrate, alpha-ketopentanoate, alpha-keto-3-methyl-butyrate, alpha-keto-4-methyl-pentanoate or alpha-keto-hexanoate in a pharmaceutically acceptable inert carrier substrate,
   wherein the condition is selected from the group consisting of rheumatoid spondylitis, osteoarthritis, gouty arthritis, endotoxic shock, cerebral malaria, silicosis, pulmonary sarcoidosis, bone resorption disease, graft versus host disease, allograft rejections, fever and myalgia due to infection, AIDS related complex (ARC), Crohn's disease, rheumatoid arthritis, cachexia and septic shock.

2. The method of claim 1, wherein said ester is an ester of pyruvic acid.

3. The method of claim 1, wherein said carrier further includes a biologically safe component for inducing and stabilizing enolization of the alpha-keto functionality of said ester at physiological pH values.

4. The method of claim 3, wherein said component for inducing and stabilizing enolization of the alpha-keto functionality of said ester is an inorganic, divalent cation.

5. The method of claim 4, wherein said divalent cation is calcium or magnesium.

6. The method of claim 1, wherein said alpha-ketoalkanoic acid ester is ethyl pyruvate, and wherein the composition further includes calcium, and said inert carrier substance is Ringer's solution in a pH range of 7–8.

7. The method of claim 1, wherein said inert carrier is a Ringer's solution of isotonic saline supplemented with potassium ion.

8. The method of claim 1, wherein said ester of an alpha-ketoalkanoic acid compound is admixed in a saline solution, said solution containing a cation selected from the group consisting of calcium and magnesium.

9. A method for treating a cytokine-mediated inflammatory condition in a patient suffering therefrom, comprising:

administering to said patient an affective amount of a composition comprising an ester of an acid selected from the group consisting of alpha-keto-propionic acid (pyruvate), alpha-keto-butyrate, alpha-keto-pentanoate, alpha-keto-3-methyl-butyrate, alpha-keto-4-methyl-pentanoate and alpha-keto-hexanoate in a pharmaceutically acceptable inert carrier.

10. A method for treating a cytokine-mediated inflammatory condition in a patient suffering therefrom, comprising:

orally, intranasally, subcutaneously, intramuscularly, intravenously, intralumenally or intra-arterially administering to said patient an effective amount of a composition comprising an ester of an acid selected from the group consisting of ketopropionic acid (pyruvate), alpha-keto-butyrate, alpha-ketopentanoate, alpha-keto-3-methyl-butyrate, alpha-keto-4-methyl-pentanoate and alpha-keto-hexanoate, and, optionally, pharmaceutically safe organic or inorganic cations in a pharmaceutically acceptable inert carrier.

11. The method of claim 10 wherein the ester is an ethyl ester.

12. The method of claim 10 wherein the ester is ethyl pyruvate.

13. The method of claim 10, wherein said composition is administered up to 24 hours after onset of said inflammatory condition.

14. The method of claim 10, wherein said carrier further comprises a biologically safe component for inducing and stabilizing enolization of the alpha-keto functionality of said acid at physiological pH values.

15. The method of claim 14, wherein said component for inducing and stabilizing enolization of the alpha-keto functionality of said ester is an inorganic, divalent cation.

16. The method of claim 15, wherein said divalent cation is calcium or magnesium.

17. The method of claim 10, wherein said inert carrier is Ringer's solution in a pH range of 7–8.

18. The method of claim 10, wherein said inert carrier is a Ringer's solution of isotonic saline supplemented with potassium ion.

19. The method of claim 10, wherein the ester is admixed in a saline solution, said solution containing a cation selected from the group consisting of calcium and magnesium.

20. The method of claim 10, wherein said inflammatory condition is inflammatory bowel disease, rheumatoid arthritis, asthma, sepsis or septic shock.

21. A method for treating a cytokine-mediated inflammatory condition in a patient suffering therefrom, said method comprising:

administering to said patient an effective amount of a composition comprising ethyl pyruvate in a pharmaceutically acceptable inert carrier substance, wherein the condition is selected from the group consisting of rheumatoid spondylitis, osteoarthritis, gouty arthritis, endotoxic shock, cerebral malaria, silicosis, pulmonary sarcoidosis, bone resorption disease, graft versus host disease, allograft rejections, fever and myalgia due to infection, AIDS related complex (ARC), Crohn's disease, rheumatoid arthritis, cachexia and septic shock.

22. A method for treating a cytokine-mediated inflammatory condition in a patient suffering therefrom, comprising:

administering to said patient an effective amount of a composition consisting essentially of an ester of an acid selected from the group consisting of ketopropionic acid (pyruvate), alpha-keto-butyrate, alpha-ketopentanoate, alpha-keto-3-methyl-butyrate, alpha-keto-4-methyl-pentanoate and alpha-keto-hexanoate, and, optionally, pharmaceutically safe organic or inorganic cations in a pharmaceutically acceptable inert carrier.

23. A method for treating a cytokine-mediated inflammatory condition in a patient suffering therefrom, comprising:

administering to said patient an effective amount of a composition consisting essentially of ethyl pyruvate in a pharmaceutically acceptable inert carrier.

* * * * *